US010752934B2

(12) United States Patent
Wang et al.

(10) Patent No.: US 10,752,934 B2
(45) Date of Patent: Aug. 25, 2020

(54) PQQ-SGDH MUTANT, POLYNUCLEOTIDE AND GLUCOSE DETECTION BIOSENSOR

(71) Applicant: LEADWAY (HK) LIMITED, Hong Kong (CN)

(72) Inventors: Zhe Wang, Zhejiang (CN); Xin Bi, Zhejiang (CN); Riyong Qiu, Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 198 days.

(21) Appl. No.: 15/771,986

(22) PCT Filed: Oct. 28, 2016

(86) PCT No.: PCT/CN2016/103858
§ 371 (c)(1),
(2) Date: Apr. 27, 2018

(87) PCT Pub. No.: WO2017/071664
PCT Pub. Date: May 4, 2017

(65) Prior Publication Data
US 2019/0390247 A1 Dec. 26, 2019

(30) Foreign Application Priority Data
Oct. 29, 2015 (CN) .......................... 2015 1 0717850

(51) Int. Cl.
*C12Q 1/54* (2006.01)
*C12N 5/16* (2006.01)
*C12Q 1/00* (2006.01)
*C12N 5/10* (2006.01)
*C12N 9/04* (2006.01)
*C12Q 1/32* (2006.01)

(52) U.S. Cl.
CPC ................ *C12Q 1/54* (2013.01); *C12N 5/16* (2013.01); *C12Q 1/006* (2013.01); *C12Q 1/32* (2013.01); *C12Y 101/05002* (2013.01)

(58) Field of Classification Search
CPC . C12Q 1/32; C12Q 1/006; C12Q 1/54; C12N 5/16; C12Y 101/05002
See application file for complete search history.

(56) References Cited

U.S. PATENT DOCUMENTS

| 7,037,698 | B2 | 5/2006 | Suzumura et al. |
| 7,244,581 | B2 | 7/2007 | Sode |
| 7,244,600 | B2 | 7/2007 | Sode et al. |
| 7,432,096 | B2 | 10/2008 | Meissner et al. |
| 7,547,535 | B2 | 6/2009 | Kratzsch et al. |
| 7,732,179 | B2 | 6/2010 | Boenitz-Dulat et al. |
| 8,329,439 | B2 * | 12/2012 | Sode ..................... C12N 9/0006 435/14 |
| 8,580,547 | B2 | 11/2013 | Weichel et al. |
| 8,748,145 | B2 | 6/2014 | Mano et al. |

FOREIGN PATENT DOCUMENTS

| AU | 2006201542 A1 | 5/2006 | |
| CN | 1353759 A | 6/2002 | |
| CN | 1571841 A | 1/2005 | |
| CN | 1576365 A | 2/2005 | |
| CN | 1671839 A | 9/2005 | |
| CN | 1849392 A | 10/2006 | |
| CN | 1912132 A | 2/2007 | |
| CN | 1912133 A | 2/2007 | |
| CN | 1922478 A | 2/2007 | |
| CN | 1989241 A | 6/2007 | |
| CN | 101037677 A | 9/2007 | |
| CN | 101421396 A | 4/2009 | |
| CN | 102559624 B | 10/2013 | |
| CN | 101040044 B | 6/2014 | |
| CN | 105331591 * | 2/2016 | ............... C12N 5/10 |
| JP | H07255471 A | 10/1995 | |
| JP | H11243949 A | 9/1999 | |
| JP | 2000354495 A | 12/2000 | |
| JP | 2001346587 A | 12/2001 | |
| JP | 2003164293 A | 6/2003 | |
| JP | 2005270082 A | 10/2005 | |
| JP | 2012039949 A | 3/2012 | |
| JP | 2016116470 A | 6/2016 | |
| WO | 0234919 A1 | 5/2002 | |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Acuity Law Group, PC; Michael A. Whittaker

(57) ABSTRACT

The present invention provides a soluble pyrroloquinoline-quinone-dependent glucose dehydrogenase (PQQ-sGDH) mutant, wherein the amino acid positions thereof correspond to a wild-type PQQ-sGDH sequence of *Acinetobacter calcoaceticus* as shown in SEQ ID NO 1 comprising one of the following group of mutations: A194F, a combined mutation based on A194F, a combined mutation based on Q192A or a combined mutation based on Q192S. Said PQQ-sGDH mutant has good glucose substrate specificity and significantly reduced cross-reactivity to maltose and the like, and is suitable for detecting glucose in a sample such as blood.

19 Claims, No Drawings
Specification includes a Sequence Listing.

(56) References Cited

FOREIGN PATENT DOCUMENTS

| WO | 2006057722 | A1 | 6/2006 |
|---|---|---|---|
| WO | 2006085509 | A1 | 8/2006 |
| WO | 2006109578 | A1 | 10/2006 |
| WO | 2007118647 | A1 | 10/2007 |
| WO | 2008155924 | A1 | 12/2008 |
| WO | 201037489 | A1 | 12/2010 |
| WO | 2011012779 | A1 | 2/2011 |

OTHER PUBLICATIONS

Partial Supplementary European Search Report and Provisional Opinion dated Mar. 19, 2019.
Database UniParc [Online] Apr. 24, 2015 (Apr. 24, 2015), XP002789299, retrieved from UniProt Database accession No. UPI00061E2AAB online at: https://www.uniprot.org/uniparc/UPI00061E2AAB. (2 pages).
Database UniParc [Online] Feb. 4, 2013 (Feb. 4, 2013), XP002789300, retrieved from UniProt Database accession No. UPI0002AEC61C online at: https://www.uniprot.org/uniparc/UPI0002AEC61C. (3 pages).
First Office Action issued by SIPO in PRC Patent Application No. 201510717850.8 dated Feb. 13, 2018—incl Engl lang trans.
Response to First Office Action issued by SIPO in PRC Patent Application No. 201510717850.8 dated Jun. 25, 2018—incl Engl lang transl.
Second Office Action issued by SIPO in PRC Patent Application No. 201510717850.8 dated Oct. 19, 2018—incl Engl lang transl.
Response to Second Office Action issued by SIPO in PRC Patent Application No. 201510717850.8 dated Dec. 28, 2018—incl Engl lang transl.
Third Office Action issued by SIPO in PRC Patent Application No. 201510717850.8 dated May 9, 2019—incl Engl lang transl.
Response to Third Office Action issued by SIPO in PRC Patent Application No. 201510717850.8 dated Jul. 22, 2019—incl Engl lang transl.
Extended European Search Report and Written Opinion dated Jun. 21, 2019.

\* cited by examiner

```
                        SEQUENCE LISTING

<160> NUMBER OF SEQ ID NOS: 8

<210> SEQ ID NO 1
<211> LENGTH: 478
<212> TYPE: PRT
<213> ORGANISM: Acinetobacter calcoacelicus

<400> SEQUENCE: 1

Met Asn Lys His Leu Leu Ala Lys Ile Ala Leu Leu Ser Ala Val Gln
1               5                   10                  15
```

```
Leu Val Thr Leu Ser Ala Phe Ala Asp Val Pro Leu Thr Pro Ser Gln
            20                  25                  30

Phe Ala Lys Ala Lys Ser Glu Asn Phe Asp Lys Lys Val Ile Leu Ser
            35                  40                  45

Asn Leu Asn Lys Pro His Ala Leu Leu Trp Gly Pro Asp Asn Gln Ile
 50                  55                  60

Trp Leu Thr Glu Arg Ala Thr Gly Lys Ile Leu Arg Val Asn Pro Glu
 65                  70                  75                  80

Ser Gly Ser Val Lys Thr Val Phe Gln Val Pro Glu Ile Val Asn Asp
                 85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
            115                 120                 125

Ser Thr Asp Lys Glu Leu Pro Asn Gln Thr Ile Ile Arg Arg Tyr Thr
130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
            195                 200                 205

Gln Glu Leu Asn Gly Lys Asp Tyr His Thr Tyr Met Gly Lys Val Leu
            210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Glu Gln Gly Pro
            260                 265                 270

Asn Ser Asp Asp Glu Ile Asn Leu Ile Val Lys Gly Gly Asn Tyr Gly
            275                 280                 285

Trp Pro Asn Val Ala Gly Tyr Lys Asp Asp Ser Gly Tyr Ala Tyr Ala
            290                 295                 300

Asn Tyr Ser Ala Ala Asn Lys Ser Ile Lys Asp Leu Ala Gln Asn
305                 310                 315                 320

Gly Val Lys Val Ala Ala Gly Val Pro Val Thr Lys Glu Ser Glu Trp
                325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Met Thr Tyr Ile
            355                 360                 365

Cys Trp Pro Thr Val Ala Pro Ser Ser Ala Tyr Val Tyr Lys Gly Gly
            370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Leu Asp Pro Thr Tyr Ser Thr
                405                 410                 415

Thr Tyr Asp Ala Val Pro Met Phe Lys Ser Asn Asn Arg Tyr Arg
            420                 425                 430
```

```
Asp Val Ile Ala Ser Pro Asp Gly Asn Val Leu Tyr Val Leu Thr Asp
            435                 440                 445

Thr Ala Gly Asn Val Gln Lys Asp Asp Gly Ser Val Thr Asn Thr Leu
        450                 455                 460

Glu Asn Pro Gly Ser Leu Ile Lys Phe Thr Tyr Lys Ala Lys
465                 470                 475

<210> SEQ ID NO 2
<211> LENGTH: 1434
<212> TYPE: DNA
<213> ORGANISM: Acinetobacter calcoacelicus

<400> SEQUENCE: 2
atgaataaac atttattggc taaaattgct ttattaagcg ctgttcagct agttacactc      60
tcagcatttg ctgatgttcc tctaactcca tctcaatttg ctaaagcgaa atcagagaac    120
tttgacaaga aagttattct atctaatcta ataagccgc atgctttgtt atggggacca     180
gataatcaaa tttggttaac tgagcgagca acaggtaaga ttctaagagt taatccagag    240
tcgggtagtg taaaaacagt ttttcaggta ccagagattg tcaatgatgc tgatgggcag    300
aatggtttat taggttttgc cttccatcct gattttaaaa ataatcctta tatctatatt    360
tcaggtacat ttaaaaatcc gaatctaca gataaagaat taccgaacca acgattatt     420
cgtcgttata cctataataa atcaacagat acgctcgaga agccagtcga tttattagca    480
ggattacctt catcaaaaga ccatcagtca ggtcgtcttg tcattgggcc agatcaaaag    540
atttattata cgattggtga ccaagggcgt aaccagcttg cttatttgtt cttgccaaat    600
caagcacaac atacgccaac tcaacaagaa ctgaatggta aagactatca cacctatatg    660
ggtaaagtac tacgcttaaa tcttgatgga agtattccaa aggataatcc aagtttttaac   720
ggggtggtta gccatattta tacacttgga catcgtaatc cgcagggctt agcattcact    780
ccaaatggta attattgca gtctgaacaa ggcccaaact ctgacgatga attaacctc      840
attgtcaaag gtggcaatta tggttggccg aatgtagcag gttataaaga tgatagtggc    900
tatgcttatg caaattattc agcagcagcc aataagtcaa ttaaggattt agctcaaaat    960
ggagtaaaag tagccgcagg ggtccctgtg acgaaagaat ctgaatggac tggtaaaaac   1020
tttgtcccac cattaaaaac tttatatacc gttcaagata cctacaacta taacgatcca   1080
acttgtggag agatgaccta catttgctgg ccaacagttg caccgtcatc tgcctatgtc   1140
tataagggcg gtaaaaaagc aattactggt tgggaaaata cattattggt tccatcttta   1200
aaacgtggtg tcattttccg tattaagtta gatccaactt atagcactac ttatgatgac   1260
gctgtaccga tgtttaagag caacaaccgt tatcgtgatg tgattgcaag tccagatggg   1320
aatgtcttat atgtattaac tgatactgcc ggaaatgtcc aaaaagatga tggctcagta   1380
acaaatacat tagaaaaccc aggatctctc attaagttca cctataaggc taag         1434

<210> SEQ ID NO 3
<211> LENGTH: 50
<212> TYPE: DNA
<213> ORGANISM: Artificial Sequence
<220> FEATURE:
<223> OTHER INFORMATION: Synthetic primer

<400> SEQUENCE: 3
tgaccaaggg cgtaaccagc ttttctattt gttcttgcca aatcaagcac                 50

<210> SEQ ID NO 4
```

```
<211> LENGTH: 50
<212> TYPE: DNA
<213> ORGANISM: Artificial Sequence
<220> FEATURE:
<223> OTHER INFORMATION: Synthetic primer

<400> SEQUENCE: 4
gtgcttgatt tggcaagaac aaatagaaaa gctggttacg cccttggtca          50

<210> SEQ ID NO 5
<211> LENGTH: 46
<212> TYPE: DNA
<213> ORGANISM: Artificial Sequence
<220> FEATURE:
<223> OTHER INFORMATION: Synthetic primer

<400> SEQUENCE: 5
attggtgacc aagggcgtaa cgcgcttgct tatttgttct tgccaa              46

<210> SEQ ID NO 6
<211> LENGTH: 46
<212> TYPE: DNA
<213> ORGANISM: Artificial Sequence
<220> FEATURE:
<223> OTHER INFORMATION: Synthetic primer

<400> SEQUENCE: 6
ttggcaagaa caaataagca agcgcgttac gcccttggtc accaat              46

<210> SEQ ID NO 7
<211> LENGTH: 43
<212> TYPE: DNA
<213> ORGANISM: Artificial Sequence
<220> FEATURE:
<223> OTHER INFORMATION: Synthetic primer

<400> SEQUENCE: 7
tggtgaccaa gggcgtaact cgcttgctta tttgttcttg cca                 43

<210> SEQ ID NO 8
<211> LENGTH: 43
<212> TYPE: DNA
<213> ORGANISM: Artificial Sequence
<220> FEATURE:
<223> OTHER INFORMATION: Synthetic primer

<400> SEQUENCE: 8
tggcaagaac aaataagcaa gcgagttacg cccttggtca cca                 43
```

PQQ-SGDH MUTANT, POLYNUCLEOTIDE AND GLUCOSE DETECTION BIOSENSOR

CROSS-REFERENCE TO RELATED MATTERS

The present invention is filed under 35 U.S.C. § 371 as the U.S. national phase of International Patent Application No. PCT/CN2016/103858, filed Oct. 28, 2016, which designated the United States and claims priority to Chinese Patent Application No. 201510717850.8, filed Oct. 29, 2015, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Oct. 15, 2018, is named ACON-011-US_SeqListing.txt and is 8 kilobytes in size.

TECHNICAL FIELD

The present invention relates to a soluble pyrroloquinoline quinone-dependent glucose dehydrogenase (PQQ-sGDH) mutant, in particular to a series of PQQ-sGDH mutants having good substrate specificity to glucose and/or thermal stability and significantly reduced cross-reactivity to maltose, as obtained by performing a site-directed mutation through PCR amplification, with a gene encoding a wild-type PQQ-sGDH enzyme from $A.$ $calcoaceticus$ or a DNA from other microorganisms as a template, wherein a protein encoded by the DNA has at least 90% homology to the amino acid sequence of the enzyme. Also provided is a polynucleotide encoding said PQQ-sGDH mutant, an expression vector containing said polynucleotide, a transformed cell containing said expression vector, and a method, a reagent and a biosensor for detecting glucose in a sample using said PQQ-sGDH mutant.

BACKGROUND

Blood glucose concentration is a very important indicator of diabetes. Determination of blood glucose concentration is extremely important for clinical diagnosis and management of diabetes. Detection of blood glucose generally involves glucose oxidation catalyzed by an enzyme. The enzyme can be divided into glucose oxidase (GOD) and glucose dehydrogenase (GDH) according to enzyme types. When blood glucose is detected by means of a test strip and a glucometer, although GOD has a relatively higher specificity and is not interfered by sugars other than glucose, GOD is highly susceptible to oxygen in the blood, thereby resulting in an inaccurate measurement result. However, GDH is not interfered by oxygen in the blood, and thus are widely applied.

For GDH, it can be roughly classified into pyrroloquinoline quinone-dependent glucose dehydrogenase (PQQ-GDH), flavin adenine dinucleotide-dependent glucose dehydrogenase (FAD-GDH) and nicotinamide adenine dinucleotide-dependent glucose dehydrogenase (NAD-GDH) according to differences in coenzymes of GDH. As one of GDHs, PQQ-GDH uses pyrroloquinoline quinone (PQQ) as a coenzyme.

The EC number of PQQ-GDH was previously EC 1.1.99.17, and was later changed to EC 1.1.5.2. Currently, scientists have found two types of PQQ-GDH (EC 1.1.5.2) in bacteria: the first is a membrane-bound PQQ-GDH (PQQ-mGDH); and the second is a soluble PQQ-GDH (PQQ-sGDH). The biochemical properties of these two PQQ-GDHs are quite different. PQQ-sGDH is only found in the periplasmic space of $Acinetobacter$ bacteria, such as $A.$ $calcoacelicus$ and $A.$ $baumannii$, with $A.$ $calcoacelicus$ as an example for illustration hereafter.

$A.$ $calcoacelicus$ contains the aforementioned two different PQQ-GDHs, wherein PQQ-mGDH is active only in bacterial cells, and PQQ-sGDH only shows activity outside bacterial cells. Moreover, there is no significant homology between their sequences. PQQ-sGDH is composed of two identical subunits, each containing 3 calcium ions and having a molecular weight of 50 kD, wherein the N-terminus of each subunit is a signal peptide composed of 24 amino acid residues, and the signal peptide is excised after being secreted into the periplasmic space. PQQ-sGDH can catalyze the oxidation of various monosaccharides and disaccharides into corresponding ketones, the ketones are further hydrolyzed to aldonic acids, and this enzyme can provide the electrons generated during the oxidation reaction to phenazine methosulfate (PMS), 2,6-dichlorophenolindophenol (DCIP), Wurster's blue, and short-chain ubiquinone molecules such as ubiquinone Q1 and ubiquinone Q2, and certain artificial electron acceptors such as N-methylphenazonium methyl sulfate, and conductive polymers, etc. As compared with PQQ-mGDH, PQQ-sGDH has good water solubility and a wider range of electron-acceptor specificity, and thus it is well-suited for use in glucose determination with a test strip or a glucometer.

However, the wild-type PQQ-sGDH of $A.$ $calcoaceticus$ also has its own drawback, namely poor substrate specificity: it can not only oxidize glucose, but also oxidize monosaccharide and disaccharide molecules (such as maltose, galactose, lactose, mannose, xylose and ribose) through oxidation reactions. Such reactivity may cause some patients with diabetes to obtain wrong measurement values when measuring their own blood glucose levels. In particular, when diabetic patients are subjected to an intravenous injection of a formulation including maltose, galactose or xylose, or an icodextrin-based peritoneal dialysis, the blood glucose level measured through a glucometer with use of PQQ-sGDH as an oxidase may erroneously rise, and if these patients are treated according to the wrong blood glucose level, it may result in abnormal hypoglycemia, coma and even death.

SUMMARY

In view of the drawbacks of the prior art, the present invention obtains a PQQ-sGDH mutant through a site-directed mutation based on a gene encoding a wild-type PQQ-sGDH enzyme from $A.$ $calcoaceticus$ or a DNA from other microorganisms, wherein a protein encoded by the DNA has more than 90% homology to the amino acid sequence of the enzyme, and the mutant has good substrate specificity to glucose and has significantly reduced cross-reactivity to sugars such as maltose, and when the mutant is used for testing glucose in a sample such as blood, the accuracy of the measured glucose value is significantly improved.

The wild-type PQQ-sGDH was first isolated from $A.$ $calcoaceticus$ strain LMD79.41, with its amino acid sequence and DNA sequence respectively given in SEQ ID NO 1 and SEQ ID NO 2.

The "homology" referred to in the present invention means that the wild-type PQQ-sGDH derived from a microorganism other than $A.$ $calcoaceticus$ has at least 90% identity with SEQ ID NO 1 in respect of the amino acid sequence. For example, the wild-type PQQ-sGDH of *A. baumannii* meets this condition, and its wild-type amino acid sequence has been disclosed in Chinese patent application CN200610067817.6. This homology can be determined through an amino acid sequence alignment performed by using the ClustalW software.

The "numbering of amino acid positions" of the present invention is calculated based on the wild-type PQQ-sGDH sequence SEQ ID NO 1 of *A. calcoaceticus*. As for the numbering of amino acid positions of wild-type PQQ-sGDH from other microorganisms (e.g., *A. baumannii*), an amino acid sequence alignment can be performed through the ClustalW software to find out the corresponding relationship between the numberings of amino acid positions of the two bacteria. For ease of description, the present invention uses only the SEQ ID NO 1 for numbering of amino acid positions.

In the present invention, symbols such as "A194F" each represent a substitution mutation. Taking A194F as an example for illustration, it means that alanine (Ala, A) at position 194 is substituted with phenylalanine (Phe, F). Also taking N452X as an example, it means that asparagine (Asn, N) at position 452 is substituted with any amino acid (X) other than N, namely X is any amino acid selected from the group consisting of alanine (Ala, A), arginine (Arg, R), aspartic acid (Asp, D), cysteine (Cys, C), glutamine (Gln, Q), glutamic acid (Glu, E), histidine (His, H), isoleucine (Ile, I), glycine (Gly, G), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y) or valine (Val, V).

In the present invention, symbols such as "A194F+M365V" each represent a combined substitution mutation. Taking A194F+M365V as an example, it means that A at position 194 is substituted with F and M at position 365 is substituted with V, wherein "+" refers to that the two substitution mutations before and after "+" occur simultaneously.

The object of the present invention is to provide a soluble pyrroloquinoline quinone-dependent glucose dehydrogenase (PQQ-sGDH) mutant, said PQQ-sGDH mutant derived from a wild-type PQQ-sGDH amino acid sequence SEQ ID NO 1 of *A. calcoaceticus*, or derived from a wild-type amino acid sequence of other microorganisms having at least 90% homology to SEQ ID NO 1, the numbering of amino acid positions of said PQQ-sGDH mutant corresponding to that of the wild-type PQQ-sGDH amino acid sequence SEQ ID NO 1 from *A. calcoaceticus*, which is characterized in that a mutation carried by said PQQ-sGDH mutant includes: (1) A194F, or (2) one mutation selected from Q192A or Q192S, and said PQQ-sGDH mutant also includes a substitution mutation occurring at at least one of positions 99, 170, 193, 270, 318, 365, 366, 367, 372, 402, 452 and 455.

Furthermore, the mutation carried by said PQQ-sGDH mutant includes: a substitution mutation occurring at at least one of positions 99, 167, 170, 192, 193, 270, 318, 365, 366, 367, 372, 402, 452 and 455 of said PQQ-sGDH mutant on the basis of (1); or substitution mutations occurring at at least two of positions 99, 167, 170, 193, 270, 318, 365, 366, 367, 372, 402, 452 and 455 of said PQQ-sGDH mutant on the basis of (2).

Furthermore, the mutation carried by said PQQ-sGDH mutant includes a mutation selected from a group consisting of: substitution mutations occurring at at least two of positions 99, 167, 170, 193, 270, 318, 365, 366, 367, 372, 402, 452 and 455 of said PQQ-sGDH mutant on the basis of (1);

Q192A+G99X+D167X+N452X;
Q192S+G99X+D167X+N452X;
Q192A+G99X+S170X+Q270X+M365X+N452X+T372X;
Q192A+G99X+S170X+Q270X+T366X+N452X+T372X;
Q192A+G99X+S170X+Q270X+T366X+N452X+R402X;
Q192A+G99X+S170X+Q270X+T366X+N452X+A318X;
Q192A+G99X+S170X+Q270X+T366N+K455X+T372X;
Q192S+G99X+S170X+Q270X+M365X+N452X+T372X;
Q192S+G99X+S170X+Q270X+T366X+N452X+T372X;
Q192S+G99X+S170X+Q270X+T366X+N452X+R402X;
Q192S+G99X+S170X+Q270X+T366X+N452X+A318X; and
Q192S+G99X+S170X+Q270X+T366N+K455X+T372X.

Furthermore, the mutation carried by said PQQ-sGDH mutant includes a mutation selected from a group consisting of:
A194F+G99X+D167X+N452X;
A194F+G99X+S170X+Q270X+T366N+N452X+T372X;
A194F+G99X+S170X+Q270X+T366N+N452X+R402X;
A194F+G99X+S170X+Q270X+T366N+N452X+A318X;
A194F+G99X+S170X+Q270X+T366N+K455X+T372X;
Q192A+G99X+D167X+N452X+M365X;
Q192A+G99X+D167X+N452X+T366X;
Q192A+G99X+S170X+Q270X+M365X+T366X+N452X+T372X;
Q192A+G99X+S170X+Q270X+T366N+N452X+K455X+T372X;
Q192S+G99X+D167X+N452X+M365X;
Q192S+G99X+D167X+N452X+T366X;
Q192S+G99X+S170X+Q270X+M365X+T366X+N452X+T372X; and
Q192S+G99X+S170X+Q270X+T366N+N452X+K455X+T372X.

Furthermore, the mutation carried by said PQQ-sGDH mutant includes a mutation selected from a group consisting of:
A194F+G99X+D167X+N452X+M365X;
A194F+G99X+D167X+N452X+T366X;
A194F+G99X+S170X+Q270X+T366N+N452X+K455X+T372X;
Q192A+G99X+D167X+N452X+T366X+S170X;
Q192A+G99X+S170X+Q270X+M365X+T366N+N452X+K455X+T372X;
Q192S+G99X+D167X+N452X+T366X+S170X; and
Q192S+G99X+S170X+Q270X+M365X+T366N+N452X+K455X+T372X.

Furthermore, the mutation carried by the PQQ-sGDH mutant includes a mutation selected from a group consisting of:
A194F+G99X+D167X+N452X+T366X+S170X;
Q192A+G99X+D167X+N452X+T366X+S170X+Q270X; and
Q192S+G99X+D167X+N452X+T366X+S170X+Q270X.

Furthermore, the mutation carried by the PQQ-sGDH mutant includes
A194F+G99X+D167X+N452X+T366X+S170X+Q270X.

Furthermore, if the mutation carried by said PQQ-sGDH mutant includes position 99, then G at position 99 can be substituted with any amino acid (X) other than G, wherein X is preferably W.

If the mutation carried by said PQQ-sGDH mutant includes position 167, then D at the position 167 can be substituted with any amino acid (X) other than D, wherein X is preferably E.

If the mutation carried by said PQQ-sGDH mutant includes position 170, then S at position 170 can be substituted with any amino acid (X) other than S, wherein X is preferably G.

If the mutation carried by said PQQ-sGDH mutant includes position 192, then Q at position 192 can be substituted with any amino acid (X) other than Q, wherein preferably, X is A or S; and most preferably, X is S.

If the mutation carried by said PQQ-sGDH mutant includes position 193, then L at position 193 can be substituted with any amino acid (X) other than L, wherein X is preferably P or F. If the mutation carried by said PQQ-sGDH mutant includes position 270, then Q at position 270 can be substituted with any amino acid (X) other than Q, wherein X is preferably H.

If the mutation carried by said PQQ-sGDH mutant includes position 318, then A at position 318 can be substituted with any amino acid (X) other than A, wherein X is preferably D.

If the mutation carried by said PQQ-sGDH mutant includes position 365, then M at position 365 can be substituted with any amino acid (X) other than M, wherein X is preferably V.

If the mutation carried by said PQQ-sGDH mutant includes position 366, then T at position 366 can be substituted with any amino acid (X) other than T, wherein X is preferably N or V.

If the mutation carried by said PQQ-sGDH mutant includes position 367, then Y at position 367 can be substituted with any amino acid (X) other than Y, wherein X is preferably C or S.

If the mutation carried by said PQQ-sGDH mutant includes position 372, then T at position 372 can be substituted with any amino acid (X) other than T, wherein X is preferably S, G, C or D.

If the mutation carried by said PQQ-sGDH mutant includes position 402, then R at position 402 can be substituted with any amino acid (X) other than R, wherein X is preferably I.

If the mutation carried by said PQQ-sGDH mutant includes position 452, then N at position 452 can be substituted with any amino acid (X) other than N, wherein X is preferably T, P, V, C, L, D, I or A.

If the mutation carried by said PQQ-sGDH mutant includes position 455, then K at position 455 can be substituted with any amino acid (X) other than K, wherein X is preferably R or I.

The object of the present invention is also to provide an isolated polynucleotide encoding said PQQ-sGDH mutant. Said polynucleotide is a gene sequence encoding said PQQ-sGDH mutant.

The object of the present invention is also to provide an expression vector containing said polynucleotide. The expression vector can be divided into two types, i.e., plasmid and virus (including phage).

The object of the present invention is also to provide a transformed cell containing said expression vector.

The object of the present invention is also to provide a method for preparing said PQQ-sGDH mutant, which includes: culturing said transformed cell; inducing expression of said polynucleotide in said expression vector; and isolating and purifying said PQQ-sGDH mutant.

The object of the present invention is also to provide a method for detecting glucose in a sample using said PQQ-sGDH mutant, which includes: enzymatically reacting said PQQ-sGDH mutant with glucose in the sample; and detecting a signal generated by the enzymatic reaction.

The object of the present invention is also to provide a reagent for detecting glucose in a sample, which comprises said PQQ-sGDH mutant.

The object of the present invention is also to provide a biosensor for detecting glucose in a sample, which comprises said PQQ-sGDH mutant.

DETAILED DESCRIPTION

The present invention obtains a series of PQQ-sGDH mutants by performing a site-directed mutation through PCR amplification, with a gene encoding a wild-type PQQ-sGDH enzyme from *A. calcoaceticus* LMD79.41 or a DNA from other microorganisms as a template, wherein a protein encoded by the DNA has at least 90% homology to the amino acid sequence of the enzyme. By detecting and comparing the enzymatic activities of the wild-type PQQ-sGDH and various PQQ-sGDH mutants to sugar molecules such as glucose and maltose under the same conditions, the inventors unexpectedly discovered some PQQ-sGDH mutants with superior properties, and these mutants have significantly improved substrate specificity to glucose, and also have significantly reduced cross-reactivity to sugar molecules such as maltose.

To facilitate calculation and comparison of substrate specificity or cross-reactivity of various PQQ-sGDH mutants and the wild-type PQQ-sGDH, the measured enzymatic activity to glucose as a substrate is defined as 100%, and the measured enzymatic activity to a sugar molecule other than glucose (such as maltose, galactose, etc.) is measured and compared with the former. Based on these measurement results, the substrate specificity or cross-reactivity of various PQQ-sGDH mutants and the wild-type PQQ-sGDH can be evaluated.

It is known that there are many methods for detecting enzymatic activity of the PQQ-sGDH mutants and the wild-type PQQ-sGDH, for example by detecting their enzymatic activity using reagents PMS and DCIP.

The percentage of cross-reactivity of the wild-type PQQ-sGDH to a sugar molecule other than glucose is calculated as shown in Equation 1:

cross-reactivity of wild-type PQQ-sGDH [%]=(enzymatic activity of wild-type PQQ-sGDH to sugar molecule other than glucose/enzymatic activity of wild-type PQQ-sGDH to glucose)×100%  (Equation 1)

The percentage of cross-reactivity of each of the PQQ-sGDH mutants to a sugar molecule other than glucose is calculated as shown in Equation 2:

cross-reactivity of PQQ-sGDH mutant [%]=(enzymatic activity of PQQ-sGDH mutant to sugar molecule other than glucose/enzymatic activity of PQQ-sGDH mutant to glucose)×100%  (Equation 2)

Meanwhile, in order to distinctly show that the cross-reactivity of each PQQ-sGDH mutant with sugar molecules such as maltose and galactose is significantly improved as compared with that of the wild-type PQQ-sGDH, the improvement extent of substrate specificity of each PQQ-sGDH mutant can be calculated according to Equation 3:

$$\text{Improved Substrate Specificity} = \frac{\text{Enzymatic Activity of Mutant to Glucose}}{\text{Enzymatic Activity of Wild-Type to Glucose}} \times \frac{\text{Enzymatic Activity of Wild-Type to Other Sugar Molecule}}{\text{Enzymatic Activity of Mutant to Other Sugar Molecule}} \quad \text{(Equation 3)}$$

After performing an appropriate mathematical transformation of Equation 3, it can be known that the improved substrate specificity of each PQQ-sGDH mutant is essentially obtained by dividing the calculated value of Equation 1 by the calculated value of Equation 2.

Other sugar molecule as mentioned in Equations 1, 2, and 3 refers to a sugar molecule other than glucose, which interferes with clinical testing of glucose, and is preferably maltose, galactose, xylose, mannose or allose, particularly maltose or galactose.

In addition to considering the cross-reactivity and improved substrate specificity of each PQQ-sGDH mutant, another indicator for evaluating the performance of each PQQ-sGDH mutant is the thermal stability of the PQQ-sGDH mutant. That is, the obtained wild-type PQQ-sGDH and each of the PQQ-sGDH mutants are placed at 50° C. for 30 min, and then the initial enzymatic activity before the placement at 50° C. and the residual enzymatic activity after the placement at 50° C. are calculated as percentages.

The present invention discloses a method for preparing the PQQ-sGDH mutants. During preparation, a series of PQQ-sGDH mutants can be obtained through a PCR site-directed mutation method.

In order to produce the wild-type PQQ-sGDH and the PQQ-sGDH mutants mentioned above, an expression vector and a host cell can be used, and it should be ensured that the selected expression vector and the selected host cell are matched.

The expression vector used in the present invention can be divided into a prokaryotic expression vector and a eukaryotic expression vector. For the prokaryotic expression vector and the eukaryotic expression vector, differences in the prokaryotic or eukaryotic cellular hosts determine differences in corresponding expression vectors.

The prokaryotic cell most commonly used for expression of a foreign protein is *Escherichia coli, Bacillus subtilis* or the like. The commonly-used expression vector for *E. coli* is pET series vector (Novagen), pGEX series vector (Pharmacia), pQE series vector (Qiagen), pACYC series vector (Addgene), pBAD series expression vector (Invitrogen), pDEST/pREST series expression vector (Invitrogen), pTrcHis2 series expression vector (Invitrogen) or the like, and the commonly-used expression vector for *B. subtilis* is pHT01, pHT08, pHT09, pHT10, pHT43 or the like.

The eukaryotic cell most commonly used for expression of a foreign protein is yeast cell, insect cell, plant cell and mammalian cell. The yeast cell commonly used for expression of the foreign protein is a cell of *Pichia pastoris* and a cell of *Saccharomyces cerevisiae*, wherein the commonly-used expression vector for *P. pastoris* includes pPIC series vector (Invitrogen), pGAPZ/pGAPa series expression vector (Invitrogen) and pAO815 expression vector (Invitrogen); and the commonly-used expression vector for *S. cerevisiae* includes pYES series expression vector (Invitrogen), pYC series expression vector (Invitrogen) or the like.

The insect cell commonly used for expression of a foreign protein includes *Spodoptera frugiperda* cell lines Sf9 and Sf-21, *Trichoplusia ni* cell lines Tn-368 and BTI-TN-5B1-4, or the like. The expression vector used by these cell lines is a recombinant baculovirus.

The expression vector commonly used for the plant cell can be selected from derivative vectors constructed based on the Ti plasmid of *Agrobacterium tumefaciens* or the Ri plasmid of *A. rhizogenes*, and a plant virus, such as tobacco mosaic virus, potato virus X and cowpea mosaic virus, may also be used as an expression vector.

The mammalian cell commonly used for expression of a foreign protein is CHO, HEK, BHK, HeLa, COS, SP2/0, NIH3T3, or the like. A common mammalian cell expression vector includes adenovirus expression vector, pSV and pCMV series plasmid vector, poxvirus expression vector, retrovirus expression vector or the like.

Regardless of which one is selected from the above expression vectors, various methods known in the art, such as calcium chloride transformation, polyethylene glycol (PEG)-mediated protoplast transformation, electroporation, particle bombardment, micro-injection, laser injection, DEAE-dextran transfection, calcium phosphate co-precipitation transfection or artificial liposome-mediated transfection, can be used to introduce such an expression vector carrying a gene encoding a PQQ-sGDH mutant into a suitable host cell, and the resulting host cell is a transformed cell. The transformed cell is cultured under conditions that allow expression of the foreign gene, so that the desired PQQ-sGDH mutant can be produced.

Of course, a PQQ-sGDH mutant can also be obtained by in vitro translation of mRNA produced by transcription of a gene encoding the mutant, for example by inserting the gene into an appropriate expression vector and the expression vector can be used for an in vitro transcription/translation system.

Regardless of whether a transformed-cell-based expression system or an in vitro transcription/translation system is employed, after the desired PQQ-sGDH mutant protein is expressed, various conventional protein purification techniques can be used to isolate and purify the mutant, for example, by using chromatography such as ion exchange chromatography, gel filtration chromatography, and affinity chromatography.

One of the main uses of the series of PQQ-sGDH mutants obtained in the present invention is to be used in a test strip or a biosensor to detect glucose concentration in the blood of a diabetic patient. Of course, in addition to being used for detecting glucose in the blood, it can also be used for detecting glucose in a body fluid such as urine, saliva and tears.

The present invention also includes a method of detecting glucose in a sample by using a PQQ-sGDH mutant provided by the present invention, and a biosensor and a reagent used in the detection process. There are many methods, biosensors and reagents for detecting glucose by using a PQQ-sGDH enzyme in the art, but only a few examples are given here for illustration, and this does not mean that the methods, biosensors and reagents are limited to these few examples. For example, Chinese patent application CN200580005551.6 disclosed a biosensor for detecting glucose concentration in a sample. A reagent contained in the biosensor can contain a PQQ-sGDH mutant, a stabilizer for stabilizing the enzymatic activity of the PQQ-sGDH mutant, and an electron acceptor, wherein the stabilizer is preferably selected from the group consisting of trehalose, sucrose, glycerol, mannitol and ribose, and the suitable electron acceptor can be selected from potassium ferricyanide, p-benzoquinone and its derivative, phenazine methosulfate (PMS), methyl blue, ferrocene and its derivative. During the detection process, if the sample contains glucose, then the PQQ-sGDH mutant enzymatically reacts with glucose and generates electrons, and the generated electrons are transmitted to an electrode by the electron acceptor, such that the glucose concentration in the sample can be calculated by detecting the generated current value.

As another example, a method, a device and a reagent disclosed in U.S. Pat. No. 5,484,708 A can also be used for detecting glucose in a sample by steps of: adding 1-naphthol-4-sulfonic acid, a coupling agent, a buffer solution, and a sample solution containing glucose into a cuvette and mixing well; then adding a PQQ-sGDH enzyme to cause an enzymatic reaction which results in a color change; and subsequently measuring the absorbance value at a specific detection wavelength with a spectrophotometer, wherein the specific detection wavelength is related to the selected coupling agent. For example, when the coupling agent is N,N-Bis(2-hydroxyethyl)-4-nitrosoaniline, the detection wavelength is 606 nm, and when the coupling agent is 2,4,6-tribromo-3-hydroxybenzoic acid, the detection wavelength is 705 nm.

The present invention is further illustrated in the following Examples. These Examples are not intended to limit the scope of the present invention, but to provide a further understanding of the present invention. DNA extraction, cloning, PCR site-directed mutation, construction of a transfer vector, preparation of a transformed cell, protein expression and purification, and the like methods as mentioned in the following Examples are known in the art (*Molecular Cloning: A Laboratory Manual* (*Fourth Edition*) edited by Michael R. Green and Joseph Sambrook; *Current Protocols in Molecular Biology* (2015) edited by Fred M. Ausubel and Roger Bren), and appropriate modifications can be made by those of skills in the art as desired.

Example 1: Cloning and Expression of Wild-Type PQQ-sGDH in *E. coli*

A gene encoding the wild-type PQQ-sGDH of *A. calcoaceticus* strain LMD79.41 was synthesized in vitro by Nanjing GenScript Biotech Co., Ltd. and then the synthesized gene was inserted into a plasmid PET30a (available from Novagen) according to techniques known in the art to obtain a recombinant plasmid. Subsequently, 10 μl of the resulting recombinant plasmid was introduced into a host cell of *E. coli* strain BL21 to obtain *E. coli* transformed cells, and then after being cultured in 1 ml LB liquid medium at 37° C. for 1 hour, the bacteria were spread on an agar plate and grown overnight at 37° C. Bacterial spots were picked from the agar plate for DNA sequencing. Subsequently, the bacterial spots into which a recombinant plasmid was successfully introduced as confirmed by DNA sequencing were plated to 50 ml LB medium and cultured at 37° C. until the $OD_{600}$ was 1.0. 50 μl IPTG was added to induce expression of the gene encoding the wild-type PQQ-sGDH, and then after be culturing continually for 3 hours, the bacteria cells were collected.

These bacterial cells can be collected by centrifugation, and then the recombinant plasmids carrying the gene encoding the wild-type PQQ-sGDH can be isolated from these bacterial cells using QIAGEN Plasmid Midi Kit (Qiagen).

Example 2: Preparation of PQQ-sGDH Mutants Through PCR Site-Directed Mutation With the recombinant plasmids isolated in Example 1 as a starting template, A at position 194 was substituted by F through a site-directed mutation carried out by PCR amplification.

The primers for obtaining the A194F mutation are as shown in SEQ ID NO 3 and SEQ NO 4:

```
SEQ ID NO 3:
5'-TGACCAAGGGCGTAACCAGCTTTTCTATTTGTTCTTGCCAAATC
AAGCAC-3'

SEQ ID NO 4:
5'-GTGCTTGATTTGGCAAGAACAAATAGAAAAGCTGGTTACGCCCT
TGGTCA-3'.
```

With the recombinant plasmids constructed in Example 1 as a starting template, Q at position 192 was substituted by A or S through a site-directed mutation carried out by PCR amplification.

The primers for obtaining the Q192A mutation are as shown in SEQ ID NO 5 and SEQ NO 6:

```
SEQ ID NO 5:
5'-ATTGGTGACCAAGGGCGTAACGCGCTTGCTTATTTGTTCTTGCC
AA-3'

SEQ ID NO 6:
5'-TTGGCAAGAACAAATAAGCAAGCGCGTTACGCCCTTGGTCACCA
AT-3'.
```

The primers for obtaining the Q192S mutation are as shown in SEQ ID NO 7 and SEQ NO 8:

```
SEQ ID NO 7:
5'-TGGTGACCAAGGGCGTAACTCGCTTGCTTATTTGTTCTTG
CCA-3'

SEQ ID NO 8:
5'-TGGCAAGAACAAATAAGCAAGCGAGTTACGCCCTTGGTCA
CCA-3'.
```

A PCR reaction was carried out by using the aforementioned primers according to the instructions of Primerstar polymerase purchased from Takara Co., Ltd. to respectively obtain amplified products of the PQQ-sGDH mutant-encoding genes in which a single-point mutation (A194F, Q192A or Q192S) occurred. Then cloning and expression, culturing and collecting of bacterial cells were carried out according to the method of Example 1, and meanwhile the recombinant plasmids carrying the PQQ-sGDH mutant-encoding gene in which the single-point mutation occurred were obtained from the collected bacterial cells.

Next, a PCR site-directed mutation was conducted again by using the obtained recombinant plasmids carrying the PQQ-sGDH mutant encoding gene in which the single-point mutation occurred, such that one mutation selectively occurred at one of positions 99, 167, 170, 193, 270, 318, 365, 366, 367, 372, 402, 452 and 455 on the basis of A194F, Q192A or Q192S, thereby obtaining a series of combined mutations at two positions based on A194F, Q192A or Q192S. In particular, a saturation mutation was also performed on position 452. That is, N at the position 452 was substituted by A, R, D, C, Q, E, H, I, G, L, K, M, F, P, S, T, W, Y or V respectively. If it is wanted to obtain combined mutations at three positions, a mutation should occur selectively at another one of positions 99, 167, 170, 193, 270, 318, 365, 366, 367, 372, 402, 452 and 455 based on the combined mutations at two positions. Similarly, by repeating the above operation, combined mutations at four or more positions based on A194F, Q192A or Q192S can also be obtained. For each of the combined mutations described above, cloning and expression, and culturing and collecting of bacterial cells were carried out according to the method of Example 1, and meanwhile the corresponding recombinant plasmids were also obtained from the collected bacterial cells.

All of the above PQQ-sGDH mutant-encoding genes were verified by DNA sequencing.

Example 3: Purification of Wild-Type PQQ-sGDH or PQQ-sGDH Mutant

The bacterial cells collected in Example 1 (carrying the wild-type PQQ-sGDH encoding gene) or the bacterial cells collected in Example 2 (carrying the PQQ-sGDH mutant encoding gene) were first cultured at 37° C. until the $OD_{600}$ was 1.0, and then 50 μl IPTG was added to induce expression of the gene encoding the wild-type PQQ-sGDH or the PQQ-sGDH mutant. Subsequently, E. coli cells were collected from the medium by centrifugation and resuspended with phosphate buffer A (0.2M sodium chloride, 20 mM sodium dihydrogen phosphate, pH 7.0). Then the wild-type PQQ-sGDH or the PQQ-sGDH mutant contained in the cells was released by high pressure, ultrasonic or the like disruption methods, and the supernatant is collected by centrifugation, such that the obtained supernatant contains a solution of crude enzyme of the wild-type PQQ-sGDH or the PQQ-sGDH mutant.

Next, the obtained crude enzyme solution sample was loaded onto a His-tag adsorption column previously equilibrated with phosphate buffer A, and then the column was first washed with phosphate buffer B (0.2M sodium chloride, 50 mM imidazole, and 20 mM sodium dihydrogen phosphate, pH 7.0) and finally eluted with phosphate buffer C (0.5M sodium chloride, 150 mM imidazole, 20 mM sodium dihydrogen phosphate, pH 7.0), so that a high-purity enzyme solution of the wild-type PQQ-sGDH or the PQQ-sGDH mutant was obtained. The resulting enzyme solution can also be made into an enzyme powder after being dried.

Example 4: Enzymatic Activity Detection of Wild-Type PQQ-sGDH and PQQ-sGDH Mutant Reagent preparation was required before detection: reagent A: 10 mM MOPS buffer (MOPS-NaOH buffer solution containing 1 mM $CaCl_2$, at pH 7.0); reagent B: glucose solution (1.2M); reagent C: PMS solution (20 mM); reagent D: DCIP solution (4.0 mM); and reagent E: enzyme dilution (20 mM MOPS-NaOH buffer containing 1 mM $CaCl_2$ and 0.1% Triton X-100, pH 7.0).

A suitable amount of PQQ was added to the reagent A until the concentration of PQQ reached 1 mM, so as to obtain a reagent A1. The powder of the wild-type PQQ-sGDH or the PQQ-sGDH mutant in Example 3 was dissolved in deionized water until its concentration was 1 mg/ml, such that a detection enzyme solution was obtained.

In order to measure the enzymatic activity, the wild-type PQQ-sGDH or the PQQ-sGDH mutant was first activated, namely 900 μl reagent A1 and 100 μl detection enzyme solution reacted for 1 hour at room temperature for enzyme activation.

After the enzymatic activation, the enzymatic activity of the wild-type PQQ-sGDH or the PQQ-sGDH mutant was detected and the method for detecting the enzymatic activity was as follows, wherein the detection principle of the method was:

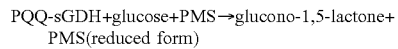

After the reaction was completed, the absorbance value (OD) at a wavelength of 600 nm was measured using a spectrophotometer. Definition: the enzymatic activity of reducing 1 μmol of DCIP by the wild-type PQQ-sGDH or the PQQ-sGDH mutant in 1 minute was 1 U.

The detailed detecting steps were as follows:
(1) The following reaction mixture was prepared in a light-proof reaction flask and stored on ice (for temporary preparation) with the following components:
2.5 ml MOPS-NaOH buffer solution (pH 7.0) concentration after mixing (17 mM)
0.3 ml glucose solution concentration after mixing (124 mM)
0.5 ml PMS solution concentration after mixing (3.45 mM)
0.5 ml DCIP solution concentration after mixing (0.69 mM)
(2) 2.9 ml of the reaction mixture was added into a test tube, placed in a water bath kettle at 25° C. and preheated for 5 min;
(3) 0.1 ml of the enzyme solution of the wild-type PQQ-sGDH or the PQQ-sGDH mutant was added, and a reverse mixing was conducted smoothly;
(4) The decline curve of OD at the wavelength of 600 nm within 5 min was plotted using a spectrophotometer under conditions of a constant temperature at 25° C. The OD change per 1 minute ($\Delta OD_{test}$) was calculated according to the straight-line portion at the beginning of the curve, and meanwhile the enzyme solution in (4) was replaced with the reagent E and a blank value ($\Delta OD_{blank}$) was determined according to the same method;
(5) The enzymatic activity was calculated:

$$U/ml=[\Delta OD/min(\Delta OD_{test}-\Delta OD_{blank})\times Vt\times df]/(22\times 1.0\times Vs),$$

$$U/mg=(U/ml)\times 1/C, \text{ wherein,}$$

Vt is the total reaction volume of 3.0 ml, and Vs is the sample volume of 0.1 ml; 22: the absorption coefficient in millimole ($cm^2$/micromole) of DCIP under the above detection conditions; 1.0: optical path; df: dilution factor, and C: enzyme concentration in a solution (mg/ml).

It should be noted that, the enzyme powder should be dissolved in the pre-cooled reagent E and diluted with the same buffer to 0.1-0.8 U/ml before testing. Moreover, a plastic tube is preferred for use in the detection due to the adhesivity of the enzyme.

Example 5: Determination of Thermal Stability of Wild-Type PQQ-sGDH or PQQ-sGDH Mutant A 20 mM potassium phosphate solution (pH 7.0) containing 1 mg of the wild-type PQQ-sGDH or the PQQ-sGDH mutant and 0.016 mg PQQ was prepared to activate the wild-type PQQ-sGDH or the PQQ-sGDH mutant. After incubation at room temperature for 30 min, the initial enzyme activity to glucose was measured according to the method of Example 4, and then after the enzyme solution was incubated in a water bath at 50° C. for 30 minutes, the residual enzyme activity of the enzyme solution was detected and calculated as a percentage.

Example 6: Cross-Reactivity and Thermal Stability Tests of Wild-Type PQQ-sGDH and PQQ-sGDH Mutant The bacterial cells collected in Example 1 or Example 2 were subjected to cell disruption by sonication. The disrupted bacterial solution was centrifuged, 100 µl of the supernatant after centrifugation was taken, and 900 µl of 10 mM MOPS buffer (pH 7.0) containing 1 mM PQQ and 1 mM $CaCl_2$ was added into the supernatant to react for 1 hour at room temperature. The holoenzyme formed after the reaction was used for the following cross-reactivity and thermal stability tests.

According to the enzymatic-activity determining method in Example 4, a certain amount of enzyme solution of the wild-type PQQ-sGDH and the PQQ-sGDH mutant was respectively taken and tested with an aqueous glucose solution having a concentration of 30 mM, and meanwhile was respectively tested with an aqueous maltose solution having a concentration of 30 mM.

During calculation of the enzymatic activity, the value obtained when 30 mM glucose was used as the substrate was set as 100% activity. The measured value for maltose was compared with the value for glucose, and the cross-reactivity [%] of the wild-type PQQ-sGDH to maltose and the cross-reactivity [%] of the PQQ-sGDH mutant to maltose were calculated according to Equation 1 and Equation 2 respectively. In the tables below, the cross-reactivity of the wild-type PQQ-sGDH or the PQQ-sGDH mutant to maltose was expressed in M/G. At the same time, based on this, the improved substrate specificity of each PQQ-sGDH mutant was calculated according to Equation 3.

The thermal stabilities of the wild-type PQQ-sGDH and the PQQ-sGDH mutants were tested as in Example 5.

(1) A194F and A194F-Based Combined Mutation

The test results of cross-reactivity and thermal stability of them were shown in Table 1:

TABLE 1

| | M/G | Relative Activity | Thermal Stability | Improved Substrate Specificity |
|---|---|---|---|---|
| Wild-type PQQ-sGDH | | | | |
| Wild Type | 104.00% | 100.00% | 90.00% | N/A |
| PQQ-sGDH mutant (A194F mutation at single position) | | | | |
| A194F | 86.46% | 17.87% | 92.20% | 1.20 |
| PQQ-sGDH mutant (A194F-based combined mutation at two positionss) | | | | |
| A194F + L193P | 22.11% | N/A | N/A | 4.70 |
| A194F + N452P | 35.52% | N/A | N/A | 2.93 |
| A194F + M365V | 35.00% | N/A | N/A | 2.97 |
| A194F + T366N | 23.44% | N/A | N/A | 4.44 |
| A194F + G99W | 30.75% | N/A | N/A | 3.38 |
| A194F + D167E | 31.48% | N/A | N/A | 3.30 |
| A194F + S170G | 27.07% | N/A | N/A | 3.84 |
| A194F + Q270H | 24.00% | N/A | N/A | 4.33 |
| A194F + T372S | 36.00% | N/A | N/A | 2.89 |
| A194F + T372G | 26.00% | N/A | N/A | 4.00 |
| A194F + T372C | 31.70% | 46.29% | 91.25% | 3.28 |
| A194F + T372D | 29.64% | 44.30% | 89.02% | 3.51 |
| A194F + R402I | 43.10% | N/A | N/A | 2.41 |
| A194F + Q192A | 14.75% | N/A | N/A | 7.05 |
| A194F + Q192S | 12.24% | N/A | N/A | 8.50 |
| PQQ-sGDH mutant (A194F-based combined mutation at three positions) | | | | |
| A194F + N452P + M365V | 27.76% | N/A | N/A | 3.75 |
| A194F + N452T + T366N | 15.31% | N/A | N/A | 6.79 |
| A194F + K455I + D167E | 26.14% | N/A | N/A | 3.98 |
| A194F + N452T + Y367C | 23.19% | N/A | N/A | 4.48 |
| A194F + N452P + D167E | 20.88% | N/A | N/A | 4.98 |
| A194F + D167E + S170G | 22.31% | N/A | N/A | 4.66 |
| A194F + G99W + Q270H | 23.33% | N/A | N/A | 4.46 |
| A194F + N452P + A318D | 12.39% | N/A | N/A | 8.39 |
| A194F + N452P + R402I | 27.82% | N/A | N/A | 3.74 |
| A194F + Q192S + N452P | 10.23% | N/A | N/A | 10.17 |
| A194F + Q192A + N452P | 8.98% | N/A | N/A | 11.58 |
| A194F + D167E + N452P | 15.75% | N/A | N/A | 6.60 |
| PQQ-sGDH mutant (A194F-based combined mutation at four or more positions) | | | | |
| A194F + D167E + N452P + G99W | 8.09% | N/A | N/A | 12.86 |
| A194F + D167E + N452P + G99W + M365V | 6.43% | N/A | N/A | 16.17 |
| A194F + D167E + N452P + G99W + T366N | 3.06% | N/A | N/A | 33.99 |
| A194F + D167E + N452P + G99W + T366N + S170G | 4.52% | N/A | N/A | 23.01 |
| A194F + D167E + N452P + G99W + T366N + S170G + Q270H | 3.11% | N/A | N/A | 33.44 |
| A194F + N452P + G99W + T366N + S170G + Q270H + T372S | 3.16% | N/A | N/A | 32.91 |
| A194F + N452P + G99W + T366N + S170G + Q270H + T372G | 2.08% | N/A | N/A | 50.00 |
| A194F + N452A + G99W + T366N + S170G + Q270H + R402I | 4.55% | N/A | N/A | 22.86 |
| A194F + N452A + G99W + T366N + S170G + Q270H + A318D | 3.41% | N/A | N/A | 30.50 |
| A194F + N452T + G99W + T366N + S170G + Q270H + T372S | 2.32% | N/A | N/A | 44.83 |
| A194F + K455I + G99W + T366N + S170G + Q270H + T372G | 2.48% | N/A | N/A | 41.94 |
| A194F + N452T + K455I + G99W + T366N + S170G + Q270H + T372G | 1.87% | N/A | N/A | 55.62 |

As could be seen from Table 1, the M/G for the single-position mutation A194F of the PQQ-sGDH mutant was 86.46% and the improved substrate specificity was 1.20, which meant that the mutant had improved substrate specificity (maltose/glucose) 1.20 times larger than that of the wild-type PQQ-sGDH. Also, the lowest M/G of the A194F-based combined mutations at two positions was 12.24%, and the lowest improved substrate specificity thereof was 2.41. Also, the lowest M/G of the A194F-based combined mutations at three positions was 8.98%, and the lowest improved substrate specificity thereof was 3.74. Also, the lowest M/G of the A194F-based combined mutations at four or more positions was 1.87%, and the lowest improved substrate specificity thereof was 12.86. It could be seen that each of the PQQ-sGDH mutants listed in Table 1 had significantly reduced cross-reactivity to maltose, and significantly increased substrate specificity to glucose.

(2) Q192A-Based Combined Mutation

The test results of cross-reactivity and thermal stability of them were shown in Table 2:

TABLE 2

|  | M/G | Relative Activity | Thermal Stability | Improved Substrate Specificity |
|---|---|---|---|---|
| Wild-type PQQ-sGDH |  |  |  |  |
| Wild Type | 104.00% | 100.00% | 90.00% | N/A |
| PQQ-sGDH mutant (Q192A-based combined mutation at two positions) |  |  |  |  |
| Q192A + L193P | 26.98% | 44.77% | 87.55% | 3.85 |
| Q192A + N452T | 32.91% | 60.50% | 81.23% | 3.16 |
| Q192A + N452P | 22.34% | 71.58% | 84.78% | 4.66 |
| Q192A + N452V | 21.25% | 51.37% | N/A | 4.89 |
| Q192A + N452C | 33.04% | 63.30% | 87.54% | 3.15 |
| Q192A + N452L | 31.27% | N/A | N/A | 3.33 |
| Q192A + N452D | 36.12% | N/A | N/A | 2.88 |
| Q192A + N452I | 40.01% | N/A | N/A | 2.60 |
| Q192A + N452A | 32.88% | N/A | N/A | 3.16 |
| Q192A + K455R | 40.55% | N/A | N/A | 2.56 |
| Q192A + K455I | 39.21% | N/A | N/A | 2.65 |
| Q192A + M365V | 25.76% | 43.19% | N/A | 4.04 |
| Q192A + T366N | 14.36% | 56.52% | 99.22% | 7.24 |
| Q192A + T366V | 16.27% | 54.14% | 89.19% | 6.39 |
| Q192A + Y367C | 19.49% | N/A | N/A | 5.34 |
| Q192A + Y367S | 27.57% | N/A | N/A | 3.77 |
| Q192A + G99W | 18.73% | N/A | N/A | 5.55 |
| Q192A + D167E | 17.80% | 42.53% | 74.60% | 5.84 |
| Q192A + S170G | 25.01% | 36.45% | N/A | 4.16 |
| Q192A + Q270H | 38.37% | 55.33% | N/A | 2.71 |
| Q192A + R402I | 40.11% | N/A | N/A | 2.59 |
| Q192A + T372S | 20.48% | 45.10% | 39.46% | 5.08 |
| Q192A + T372C | 23.30% | 30.51% | 63.90% | 4.46 |
| Q192A + T372D | 18.73% | 30.30% | 67.55% | 5.56 |
| Q192A + T372G | 15.31% | 37.84% | 30.54% | 6.79 |
| PQQ-sGDH mutant (Q192A-based combined mutations at three positions) |  |  |  |  |
| Q192 A + N452P + M365V | 25.11% | N/A | N/A | 4.14 |
| Q192A + D167E + T366N | 9.04% | N/A | N/A | 11.50 |
| Q192A + N452P + T366V | 12.99% | N/A | N/A | 8.02 |
| Q192A + N452P + Y367C | 17.76% | N/A | N/A | 5.86 |
| Q192A + K455I + Y367S | 20.43% | N/A | N/A | 5.09 |
| Q192A + N452V + T372C | 11.42% | N/A | N/A | 9.11 |
| Q192A + N452T + T372D | 12.42% | N/A | N/A | 8.37 |
| Q192A + N452P + T372S | 14.05% | N/A | N/A | 7.40 |
| Q192A + N452P + D167E | 20.67% | N/A | N/A | 5.03 |
| Q192A + D167E + S170G | 9.73% | N/A | N/A | 10.69 |
| Q192A + N452P + Q270H | 16.65% | N/A | N/A | 6.25 |
| Q192A + N452T + A318D | 17.72% | N/A | N/A | 5.87 |
| Q192A + N452T + G99W | 6.74% | N/A | N/A | 15.43 |
| Q192A + N452T + R402I | 17.38% | N/A | N/A | 5.984 |
| Q192A + D167E + N452P | 6.89% | N/A | N/A | 15.09 |
| PQQ-sGDH mutant (Q192A-based combined mutation at four positions) |  |  |  |  |
| Q192A + D167E + N452P + G99W | 5.98% | N/A | N/A | 17.39 |
| Q192A + D167E + N452P + G99W + M365V | 4.37% | N/A | N/A | 23.80 |
| Q192A + D167E + N452P + G99W + T366N | 4.51% | N/A | N/A | 23.06 |
| Q192A + D167E + N452P + G99W + T366N + S170G | 4.03% | N/A | N/A | 25.81 |
| Q192A + D167E + N452P + G99W + T366N + S170G + Q270H | 3.51% | N/A | N/A | 29.63 |
| Q192A + N452P + G99W + T366N + S170G + Q270H + T372S | 7.11% | N/A | N/A | 14.63 |
| Q192A + N452P + G99W + M365V + S170G + Q270H + T372S | 8.89% | N/A | N/A | 11.70 |
| Q192A + N452P + G99W + M365V + T366N + S170G + Q270H + T372S | 6.15% | N/A | N/A | 16.91 |
| Q192A + N452P + G99W + T366N + S170G + Q270H + T372G | 4.65% | N/A | N/A | 22.37 |
| Q192A + N452A + G99W + T366N + S170G + Q270H + R402I | 5.15% | N/A | N/A | 20.19 |
| Q192A + N452A + G99W + T366N + S170G + Q270H + A318D | 5.62% | N/A | N/A | 18.51 |
| Q192A + N452T + G99W + T366N + S170G + Q270H + T372S | 2.37% | N/A | N/A | 43.88 |

TABLE 2-continued

| | M/G | Relative Activity | Thermal Stability | Improved Substrate Specificity |
|---|---|---|---|---|
| Q192A + K455I + G99W + T366N + S170G + Q270H + T372G | 2.09% | N/A | N/A | 49.76 |
| Q192A + N452T + K455I + G99W + T366N + S170G + Q270H + T372G | 1.99% | N/A | N/A | 52.26 |
| Q192A + N452P + K455R + G99W + M365V + T366N + S170G + Q270H + T372S | 2.67% | N/A | N/A | 38.95 |

As could be seen from Table 2, the lowest M/G of the Q192A-based combined mutations at two positions was 14.36%, and the lowest improved substrate specificity thereof was 2.56. Also, the lowest M/G of the Q192A-based combined mutations at three positions was 6.74%, and the lowest improved substrate specificity thereof was 4.14. Also, the lowest M/G of the Q192A-based combined mutations at four or more positions was 1.99%, and the lowest improved substrate specificity thereof was 11.70. It could be seen that each of the PQQ-sGDH mutants listed in Table 2 had significantly reduced cross-reactivity to maltose, and significantly increased substrate specificity to glucose.

(3) Q192S-Based Combined Mutation

The test results of cross-reactivity and thermal stability of them were shown in Table 3:

TABLE 3

| | M/G | Relative Activity | Thermal Stability | Improved Substrate Specificity |
|---|---|---|---|---|
| Wild-type PQQ-sGDH | | | | |
| Wild Type | 104.00% | 100.00% | 90.00% | N/A |
| PQQ-sGDH mutant (Q192S-based combined mutation at two positions) | | | | |
| Q192S + L193P | 25.66% | 48.98% | 90.80% | 4.05 |
| Q192S + N452T | 29.13% | 61.77% | 77.41% | 3.57 |
| Q192S + N452P | 20.41% | 77.53% | 86.12% | 5.10 |
| Q192S + N452V | 19.98% | 57.49% | N/A | 5.21 |
| Q192S + N452C | 30.93% | 67.41% | 88.91% | 3.36 |
| Q192S + N452L | 36.43% | N/A | N/A | 2.85 |
| Q192S + N452D | 32.97% | N/A | N/A | 3.15 |
| Q192S + N452I | 36.20% | N/A | N/A | 2.87 |
| Q192S + N452A | 31.16% | N/A | N/A | 3.34 |
| Q192S + K455R | 37.23% | N/A | N/A | 2.79 |
| Q192S + K455I | 36.83% | N/A | N/A | 2.82 |
| Q192S + M365V | 21.65% | 49.14% | N/A | 4.80 |
| Q192S + T366N | 9.55% | 62.74% | 91.24% | 10.89 |
| Q192S + T366V | 14.12% | 53.16% | 79.97% | 7.37 |
| Q192S + Y367C | 17.84% | N/A | N/A | 5.83 |
| Q192S + Y367S | 24.10% | N/A | N/A | 4.32 |
| Q192S + G99W | 17.71% | N/A | N/A | 5.87 |
| Q192S + D167E | 16.65% | 48.77% | 69.48% | 6.25 |
| Q192S + S170G | 23.13% | 44.37% | N/A | 4.50 |
| Q192S + Q270H | 34.92% | 60.48% | N/A | 2.98 |
| Q192S + R402I | 38.44% | N/A | N/A | 2.71 |
| Q192S + T372S | 16.22% | 49.32% | 40.85% | 6.41 |
| Q192S + T372G | 14.10% | 44.29% | 33.77% | 7.38 |
| Q192S + T372C | 14.33% | 60.72% | 82.65% | 7.26 |
| Q192S + T372D | 15.63% | 61.84% | 88.04% | 6.65 |
| PQQ-sGDH mutant (Q192S-based combined mutation at three positions) | | | | |
| Q192S + D167E + M365V | 23.88% | N/A | N/A | 4.36 |
| Q192S + N452P + T366N | 8.23% | N/A | N/A | 12.64 |
| Q192S + N452T + T366V | 12.87% | N/A | N/A | 8.08 |
| Q192S + K455I + Y367C | 16.54% | N/A | N/A | 6.29 |
| Q192S + N452T + Y367S | 19.76% | N/A | N/A | 5.26 |
| Q192S + N452V + T372S | 10.28% | N/A | N/A | 10.12 |
| Q192S + N452T + T372D | 11.87% | N/A | N/A | 8.76 |
| Q192S + N452P + T372C | 12.73% | N/A | N/A | 8.17 |
| Q192S + N452P + D167E | 6.67% | N/A | N/A | 15.59 |
| Q192S + D167E + S170G | 10.37% | N/A | N/A | 10.29 |
| Q192S + N452P + Q270H | 15.42% | N/A | N/A | 6.74 |
| Q192S + G99W + A318D | 17.23% | N/A | N/A | 6.04 |
| Q192S + N452T + G99W | 6.63% | N/A | N/A | 15.69 |
| Q192S + N452T + R402I | 15.23% | N/A | N/A | 6.83 |
| Q192S + D167E + N452P | 9.06% | N/A | N/A | 11.48 |
| PQQ-sGDH mutant (Q192S-based combined mutation at four or more positions) | | | | |
| Q192S + D167E + N452P + G99W | 6.95% | N/A | N/A | 14.96 |
| Q192S + D167E + N452P + G99W + M365V | 4.50% | N/A | N/A | 23.11 |
| Q192S + D167E + N452P + G99W + T366N | 5.88% | N/A | N/A | 17.69 |
| Q192S + D167E + N452P + G99W + T366N + S170G | 6.29% | N/A | N/A | 16.53 |

TABLE 3-continued

| | M/G | Relative Activity | Thermal Stability | Improved Substrate Specificity |
|---|---|---|---|---|
| Q192S + D167E + N452P + G99W + T366N + S170G + Q270H | 4.76% | N/A | N/A | 21.85 |
| Q192S + N452P + G99W + T366N + S170G + Q270H + T372S | 6.40% | N/A | N/A | 16.25 |
| Q192S + N452P + G99W + M365V + S170G + Q270H + T372S | 8.15% | N/A | N/A | 12.76 |
| Q192S + N452P + G99W + M365V + T366N + S170G + Q270H + T372S | 5.87% | N/A | N/A | 17.72 |
| Q192S + N452P + G99W + T366N + S170G + Q270H + T372G | 4.87% | N/A | N/A | 21.36 |
| Q192S + N452A + G99W + T366N + S170G + Q270H + R402I | 6.23% | N/A | N/A | 16.69 |
| Q192S + N452A + G99W + T366N + S170G + Q270H + A318D | 6.90% | N/A | N/A | 15.07 |
| Q192S + N452T + G99W + T366N + S170G + Q270H + T372S | 3.13% | N/A | N/A | 33.23 |
| Q192S + K455I + G99W + T366N + S170G + Q270H + T372G | 2.96% | N/A | N/A | 35.14 |
| Q192S + N452T + K455I + G99W + T366N + S170G + Q270H + T372G | 1.75% | N/A | N/A | 59.43 |
| Q192S + N452P + K455R + G99W + M365V + T366N + S170G + Q270H + T372S | 2.33% | N/A | N/A | 44.64 |

As could be seen from Table 3, the lowest M/G of the Q192S-based mutations at two positions was 9.55%, and the lowest improved substrate specificity thereof was 2.98. Also, the lowest M/G of the Q192S-based combined mutations at three positions was 6.63%, and the lowest improved substrate specificity thereof was 4.36. Also, the lowest M/G of the Q192S-based combined mutations at four or more positions was 1.75%, and the lowest improved substrate specificity thereof was 12.76. It could be seen that each of the PQQ-sGDH mutants listed in Table 3 had significantly reduced cross-reactivity to maltose, and significantly increased substrate specificity to glucose.

Example 7: Maltose Interference Experiment

A glucose assay was performed with a wild-type PQQ-sGDH or a PQQ-sGDH mutant. The reference sample contained 50 mg/dl glucose. The test sample contained 50 mg/dl glucose and 100 mg/dl maltose. The same amount of enzymatic activity (U/ml; see Example 4) was used for each assay.

The test solution was prepared in advance:
1000 μl of 0.2M citric acid buffer (pH 5.8) containing 0.315 mg of (4-(dimethylphosphinylmethyl)-2-methylpyrazolo-[1.5a]-imidazol-3-yl)-(4-nitrosophenyl)-amine).

Next, 1 ml of the test solution and 0.015 ml of the reference sample or the test sample were added into a cuvette, and mixed well.

After adding 0.050 ml of 90 U/ml wild-type PQQ-sGDH or PQQ-sGDH mutant, this assay then started. The absorbance change at 620 nm was monitored. A constant value was observed after 5 min, and then the absorbance change value within 5 min was calculated. The absorbance change value obtained by measuring the reference sample with the wild-type PQQ-sGDH was set as 100%, and then the percentage of the wild-type PQQ-sGDH for measuring the test sample and the percentages of the PQQ-sGDH mutant for measuring the reference sample and the test sample were respectively calculated based on this set value. The results were shown in Table 4:

TABLE 4

| | 50 mg/dl glucose | 50 mg/dl glucose and 100 mg/dl maltose |
|---|---|---|
| Wild-type PQQ-sGDH | 100% | 160% |
| PQQ-sGDH mutant (A194F) | 100% | 121% |

It could be seen clearly from Table 4 that, the measured glucose value was significantly decreased when the PQQ-sGDH mutant (A194F) was used in the assay, which meant that as compared with the wild-type PQQ-sGDH, when the PQQ-sGDH mutant (A194F) was used for measuring glucose, the interference of the presence of maltose to the measurement results was significantly reduced.

Maltose interference experiments were conducted with other PQQ-sGDH mutants of the present invention, it was also found that the interference of the presence of maltose to the measurement results was significantly reduced as compared with the wild-type PQQ-sGDH.

Furthermore, a glucose detection biosensor disclosed in Chinese patent application CN200580005551.6 could also be used to detect the concentration of glucose in a blood sample, wherein the reaction layer of the biosensor contained the PQQ-sGDH mutant provided by the present invention, and the results meant that if maltose was present in the sample, the accuracy of numerical values detected with any one of the PQQ-sGDH mutants provided by the present invention was significantly increased as compared to the wild-type PQQ-sGDH, and the interference of the maltose in the sample to the measurement results was significantly reduced.

What is claimed is:

1. A pyrroloquinoline quinone-dependent soluble glucose dehydrogenase (PQQ-sGDH) protein having at least 90% sequence identity to the entire sequence of SEQ ID NO: 1, wherein said PQQ-sGDH protein comprises the following mutations relative to SEQ ID NO: 1:
   an A194F substitution, or
   one substitution selected from Q192A or Q192S, and a substitution occurring at at least one of positions G99, S170, L193, Q270, A318, M365, T366, Y367, T372, R402, N452 and K455.

2. The PQQ-sGDH protein of claim 1, wherein the PQQ-sGDH protein comprises: an A194F substitution and a substitution occurring at at least one of positions G99, D167, S170, Q192, L193, Q270, A318, M365, T366, Y367, T372, R402, N452 and K455; or one substitution selected from Q192A or Q192S and substitutions occurring at at least two of positions G99, D167, S170, L193, Q270, A318, M365, T366, Y367, T372, R402, N452 and K455.

3. The PQQ-sGDH protein of claim 1, wherein the PQQ-sGDH protein comprises a set of substitutions selected from the group consisting of:
   an A194F substitution and substitutions occurring at at least two of positions G99, D167, S170, L193, Q270, A318, M365, T366, Y367, T372, R402, N452 and K455,
   Q192A+G99X+D167X+N452X,
   Q192S+G99X+D167X+N452X,
   Q192A+G99X+S170X+Q270X+M365X+N452X+T372X,
   Q192A+G99X+S170X+Q270X+T366X+N452X+T372X,
   Q192A+G99X+S170X+Q270X+T366X+N452X+R402X, Q192A+G99X+S170X+Q270X+T366X+N452X+A318X,
Q192A+G99X+S170X+Q270X+T366N+K455X+T372X,
Q192S+G99X+S170X+Q270X+M365X+N452X+T372X,
Q192S+G99X+S170X+Q270X+T366X+N452X+T372X,
Q192S+G99X+S170X+Q270X+T366X+N452X+R402X,
Q192S+G99X+S170X+Q270X+T366X+N452X+A318X, and
Q192S+G99X+S170X+Q270X+T366N+K455X+T372X.

4. The PQQ-sGDH protein of claim 1, wherein the PQQ-sGDH protein comprises a set of substitutions selected from the group consisting of:
A194F+G99X+D167X+N452X,
A194F+G99X+S170X+Q270X+T366N+N452X+T372X,
A194F+G99X+S170X+Q270X+T366N+N452X+R402X,
A194F+G99X+S170X+Q270X+T366N+N452X+A318X,
A194F+G99X+S170X+Q270X+T366N+K455X+T372X,
Q192A+G99X+D167X+N452X+M365X,
Q192A+G99X+D167X+N452X+T366X,
Q192A+G99X+S170X+Q270X+M365X+T366X+N452X+T372X,
Q192A+G99X+S170X+Q270X+T366N+N452X+K455X+T372X,
Q192S+G99X+D167X+N452X+M365X,
Q192S+G99X+D167X+N452X+T366X,
Q192S+G99X+S170X+Q270X+M365X+T366X+N452X+T372X, and
Q192S+G99X+S170X+Q270X+T366N+N452X+K455X+T372X.

5. The PQQ-sGDH protein of claim 1, wherein the PQQ-sGDH protein comprises a set of substitutions selected from the group consisting of:
A194F+G99X+D167X+N452X+M365X,
A194F+G99X+D167X+N452X+T366X,
A194F+G99X+S170X+Q270X+T366N+N452X+K455X+T372X,
Q192A+G99X+D167X+N452X+T366X+S170X,
Q192A+G99X+S170X+Q270X+M365X+T366N+N452X+K455X+T372X,
Q192S+G99X+D167X+N452X+T366X+S170X, and
Q192S+G99X+S170X+Q270X+M365X+T366N+N452X+K455X+T372X.

6. The PQQ-sGDH protein of claim 1, wherein the PQQ-sGDH protein comprises a set of substitutions selected from the group consisting of:
A194F+G99X+D167X+N452X+T366X+S170X,
Q192A+G99X+D167X+N452X+T366X+S170X+Q270X, and
Q192S+G99X+D167X+N452X+T366X+S170X+Q270X.

7. The PQQ-sGDH protein of claim 1, wherein the PQQ-sGDH protein comprises
A194F+G99X+D167X+N452X+T366X+S170X+Q270X.

8. The PQQ-sGDH protein of claim 3, wherein the X of the G99X is W; the X of the D167X is E; the X of the S170X is G; the X of the Q192X is A or S; the X of the L193X is P or F; the X of the Q270X is H; the X of the A318X is D; the X of the M365X is V; the X of the T366X is N or V; the X of the Y367X is C or S; the X of the T372X is S, G, C or D; the X of the R402X is I; the X of the N452X is T, P, V, C, L, D, I or A; the X of the K455X is R or I.

9. An isolated polynucleotide encoding said PQQ-sGDH protein of claim 1.

10. A biosensor for detecting glucose in a sample, wherein said biosensor comprises said PQQ-sGDH protein of claim 1.

11. The PQQ-sGDH protein of claim 4, wherein the X of the G99X is W; G; the X of the Q192X is A or S; X of the L193X is P or F; the X of the Q270X is H; the X of the A318X is D; the X of the M365X is V; the X of the T366X is N or V; the X of the Y367X is C or S; the X of the T372X is S, G, C or D; the X of the R402X is I; the X of the N452X is T, P, V, C, L, D, I or A; the X of the K455X is R or I.

12. The PQQ-sGDH protein of claim 5, wherein the X of the G99X is W; the X of the D167X is E; the X of the S170X is G; the X of the Q192X is A or S; the X of the L193X is P or F; the X of the Q270X is H; the X of the A318X is D; the X of the M365X is V; the X of the T366X is N or V; the X of the Y367X is C or S; the X of the T372X is S, G, C or D; the X of the R402X is I; the X of the N452X is T, P, V, C, L, D, I or A; the X of the K455X is R or I.

13. The PQQ-sGDH protein of claim 6, wherein the X of the G99X is W; the X of the D167X is E; the X of the S170X is G; the X of the Q192X is A or S; the X of the L193X is P or F; the X of the Q270X is H; the X of the A318X is D; the X of the M365X is V; the X of the T366X is N or V; the X of the Y367X is C or S; the X of the T372X is S, G, C or D; the X of the R402X is I; the X of the N452X is T, P, V, C, L, D, I or A; the X of the K455X is R or I.

14. The PQQ-sGDH protein of claim 7, wherein the X of the G99X is W; the X of the D167X is E; the X of the S170X is G; the X of the Q192X is A or S; the X of the L193X is P or F; the X of the Q270X is H; the X of the A318X is D; the X of the M365X is V; the X of the T366X is N or V; the X of the Y367X is C or S; the X of the T372X is S, G, C or D; the X of the R402X is I; the X of the N452X is T, P, V, C, L, D, I or A; the X of the K455X is R or I.

15. An isolated polynucleotide encoding said PQQ-sGDH protein of claim 8.

16. An isolated polynucleotide encoding said PQQ-sGDH protein of claim 11.

17. An isolated polynucleotide encoding said PQQ-sGDH protein of claim 12.

18. An isolated polynucleotide encoding said PQQ-sGDH protein of claim 13.

19. An isolated polynucleotide encoding said PQQ-sGDH protein of claim 14.

* * * * *